United States Patent [19]

Parsons et al.

[11] Patent Number: 4,772,613
[45] Date of Patent: Sep. 20, 1988

[54] FUNGICIDES

[75] Inventors: John H. Parsons, Saffron Walden; Russell G. Hunt, Harston; Susan E. Leach, Gt. Shelford; Anthony D. Buss, Trumpington; David E. Green, Linton; Michael Mellor, Haverhill; Albert Percival, Hauxton, all of England

[73] Assignee: Schering Agrochemicals Ltd., England

[21] Appl. No.: 54,191

[22] Filed: May 26, 1987

[30] Foreign Application Priority Data

May 27, 1986 [GB] United Kingdom ................. 8612976

[51] Int. Cl.$^4$ ..................... A61K 31/47; C07D 401/04
[52] U.S. Cl. ........................................ 514/309; 71/88; 71/92; 71/94; 544/356; 546/141; 546/153; 546/162; 546/167; 548/262; 548/327; 548/336
[58] Field of Search ......................... 546/141; 514/309

[56] References Cited

U.S. PATENT DOCUMENTS 3,318,906  5/1967  McKeon et al. .................... 546/141
3,594,380  7/1971  Sulkowski ........................... 546/141

Primary Examiner—Glennon H. Hollrah
Assistant Examiner—James H. Turnipseed
Attorney, Agent, or Firm—Ostrolenk, Faber, Gerb & Soffen

[57] ABSTRACT

Compounds of any of one of formulae I–VII

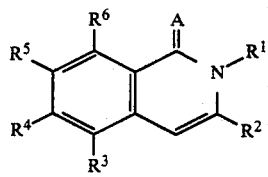

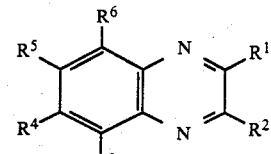

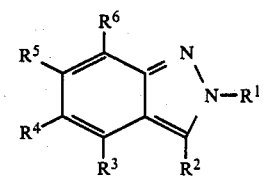

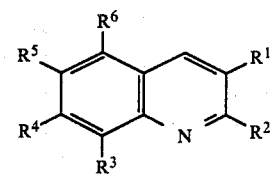

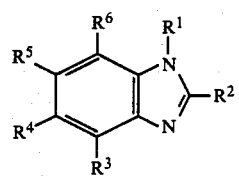

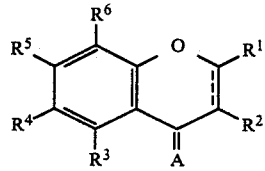

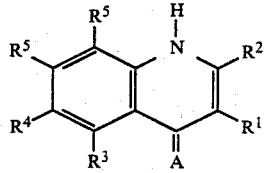

where
----- is a single or double bond;
A is oxygen or sulphur;
$R^1$ is aryl;
$R^2$ is 1-imidazolyl or 1,2,4-triazol-1-yl; and
$R^3$, $R^4$, $R^5$ and $R^6$, which may be the same or different, are each hydrogen, halo, alkyl or alkoxy, have fungicidal activity.

17 Claims, No Drawings

FUNGICIDES

This invention concerns fungicidal heterocyclic derivatives, processes for their preparation and compositions containing them.

Thre are numerous examples of imidazole and triazole derivatives having fungicidal activity. Well known products include prochloraz (BP 1469772), triadimefon (BP 1364619) and propiconazole (BP 1522657). We have now found that compounds where an imidazole or triazole group is attached to a heterocycle have valuable fungicidal properties. We are not aware of published compounds of this type having such activity.

In one aspect, the invention provides a compound of any one of formulae I-VII

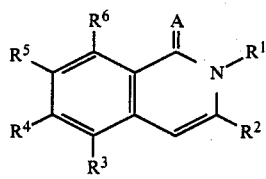

I

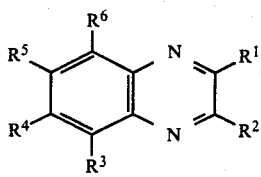

II

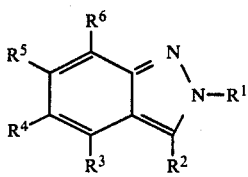

III

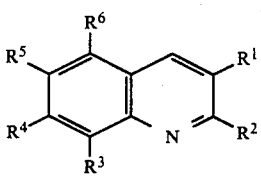

IV

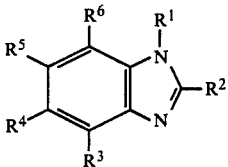

V

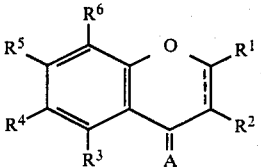

VI

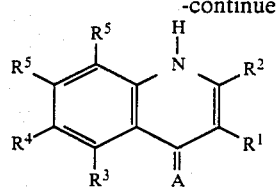

VII where
········· is a single or double bond;
A is oxygen or sulphur;
$R^1$ is aryl;
$R^2$ is 1-imidazolyl or 1,2,4-triazol-1-yl; and
$R^3$, $R^4$, $R^5$ and $R^6$, which may be the same or different, are each hydrogen, halo, alkyl or alkoxy.
A is preferably oxygen.

In the groups $R^1$, $R^3$, $R^4$, $R^5$ and $R^6$, any alkyl or alkoxy moiety is preferably of 1 to 6 carbon atoms and any aryl moiety is preferably phenyl.

$R^1$ is preferably phenyl, which may be substituted by one or more groups selected from halogen, alkyl (optionally substituted, e.g. by halogen, especially fluorine), alkoxy (optionally substituted, e.g. by halogen and especially fluorine) or nitro. Particularly preferred groups which $R^1$ may represent include phenyl, 4-chlorophenyl and 2,4-dichlorophenyl.

At least two, and preferably three or four, of $R^3$–$R^6$ desirably represent hydrogen. Where only one of $R^3$–$R^6$ is other than hydrogen, it is preferably $R^5$. Examples of groups which $R^3$–$R^6$ may represent include chloro, bromo, iodo and methyl.

Preferred compounds are those of formula I.

The compounds of formulae I-V may be prepared by reaction of the corresponding compounds where $R^2$ is halogen, usually chlorine, with 1,2,4-triazole or imidazole. The halo precursor compounds can be prepared in a variety of ways known in the art and as exemplified in the Examples. Some may be known compounds.

Compounds of formula VI can be prepared by reacting a compound of formula VIa

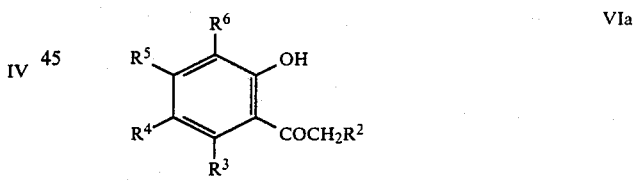

VIa with a compound of formula $$R^1COZ$$

V where Z is (i) a leaving group, such as halogen, when the bond between $R^1$ and $R^2$ is a double bond or is (ii) hydrogen when this bond is a single bond.

The compound of formula VIa can be prepared by reacting a compound of formula VIb

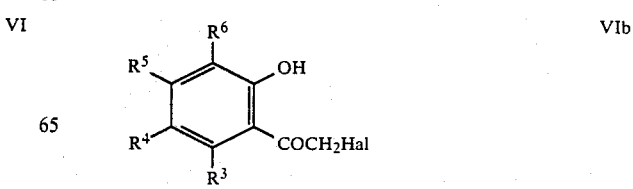

VIb where Hal is a halogen atom such as bromine, with 1,2,4-triazole or imidazole.

Reactions with 1,2,4-triazole or imidazole are usually carried out under basic conditions.

The compounds of formulae I–VII are fungicidal, possessing activity inter alia against a wide range of phytopathogenic fungi, particularly phycomycetes, deuteromycetes, ascomycetes and basidiomycetes orders, e.g. powdery mildew (*Erysiphe graminis*) on cereal crops such as wheat, barley, oats and rye and other cereal diseases such as glume blotch (*Septoria nodorum*), leaf blotch (*Rhynchosporium secalis*), eyespot (*Pseudocercosporella herpotrichoides*), rusts (e.g. *Puccinia graminis*) and take-all (*Gaeumannomyces graminis*). Some compounds of the present invention can be used to control seed borne organisms such as bunt (*Tilletia caries*) on wheat, loose smut (*Ustilago nuda* and *Ustilago hordei*) on barley and oats, leaf spot (*Pyrenophora avenae*) on oats and leaf stripe (*Pyrenophora graminis*) on barley. The compounds can be used against powdery mildews of other crops, e.g. cucumber powdery mildew (*E. cichoracearum*), apple powdery mildew (*Podosphaera leucotricha*) and vine powdery mildew (*Uncinula necator*). They can also be applied to rice for control of rice blast (*Pyricularia oryzae*) and to horticultural crops such as apple trees for the control of apple scab (*Venturia inaequalis*).

In another aspect, therefore, the invention provides a method of combating fungi at a locus infested or liable to be infested therewith, which comprises applying to the locus an effective amount of one or more compounds of formulae I–VII.

The invention also provides a method of regulating the growth of plants which comprises applying to said plants a growth regulating amount of one or more compounds of formulae I–VII.

The present compounds are normally employed in the form of compositions containing a surface active agent and/or a carrier.

The compositions will normally be produced initially containing from 0.5 to 99%, preferably from 0.5 to 85%, and more usually from 10 to 50% by weight of the present compounds, which are diluted if necessary before application to the locus to be treated such that the concentration of active ingredient in the formulation applied is from 0.05 to 5% by weight.

The carrier may be water, in which case an organic solvent may also be present, though this is not usually employed. A flowable suspension concentrate may be formed by grinding the compound with water, a wetting agent and a suspending agent, e.g. xanthan gum.

The carrier may alternatively be a water immiscible organic solvent, e.g. a hydrocarbon which boils within the range 130°–270° C., e.g. xylene, in which the compound is dissolved or suspended. An emulsifiable concentrate containing a water immiscible solvent may be formed with a surface active agent so that the concentrate acts as a self-emulsifiable oil on admixture with water.

The carrier may alternatively be a water-miscible organic solvent e.g. 2-methoxy ethanol, methanol, propylene glycol, diethylene glycol, diethylene glycol monoethyl ether, formamide or dimethylformamide.

The carrier may alternatively be a solid, which may be finely divided or granular. Examples of suitable solids are limestone, clays, sand, mica, chalk, attapulgite, diatomite, perlite, sepiolite, silicas, silicates, lignosulphonates and solid fertilizers. The carrier can be of natural or synthetic origin or can be modified natural material.

Wettable powders soluble or dispersible in water may be formed by admixing the compound in particulate form with a particulate carrier or spraying molten compound on to the particulate carrier, admixing a wetting agent and a dispersing agent and finely grinding the whole powder mixture.

The term 'surface active agent' is used in the broad sense to include materials variously called emulsifying agents, dispersing agents and wetting agents. Such agents are well known in the art.

The surface active agents used may comprise anionic surface active agents, for example mono- or di-esters of phosphoric acid with a fatty alcohol ethoxylate, or salts of such esters, fatty alcohol sulphates such as sodium dodecyl suphate, ethoxylated fatty alcohol sulphates, ethoxylated alkylphenol sulphates, lignin sulphates, petroleum sulphonates, alkylaryl sulphonates such as alkyl-benzene sulphonates or lower alkylnaphthalene sulphonates, salts of sulphonated naphthaleneformaldehyde condensates, salts of sulphonated phenolformaldehyde condensates, or more complex sulphonates such as the amide sulphonates, e.g. the sulphonated condensation product of oleic acid and N-methyl taurine or the dialkyl sulphosuccinates e.g. the sodium sulphonate of dioctyl succinate.

The surface active agents may also comprise nonionic agents, for example condensation products or fatty acid esters, fatty alcohols, fatty acid amides or alkyl-substituted phenols with ethylene oxide, fatty esters of polyhydric alcohol ethers e.g. sorbitan fatty acid esters, condensation products of such esters with ethylene oxide e.g. polyoxyethylene sorbitan fatty acid esters, block copolymers of ethylene oxide and propylene oxide, acetylenic glycols such as 2,4,7,9-tetramethyl-5-decyn-4,7-diol, or ethoxylated acetylenic glycols.

The surface active agents may also comprise cationic agents, for example alkyl- and/or aryl-substituted quaternary ammonium compounds such as cetyl trimethylammonium bromide, or ethoxylated tertiary fatty amines.

Preferred surface active agents include ethoxylated fatty alcohol sulphates, lignin sulphonates, alkyl-aryl sulphonates, salts of sulphonated naphthaleneformaldehyde condensates, salts of sulphonated phenolformaldehyde condensates, sodium oleoyl N-methyltauride, dialkyl sulphosuccinates, alkyl phenol ethoxylates, and fatty alkyl ethoxylates.

The compounds of the invention may of course be used in conjunction with one or more further active ingredients, for example compounds known to possess plant-growth regulant, herbicidal, fungicidal, insecticidal or acaricidal properties. Alternatively the compounds of the invention can be used in sequence with the other active ingredient.

In the method of the invention the compound is generally applied to seeds, plants or their habitat. Thus, the compound can be applied directly to the soil before, at or after drilling so that the presence of active compound in the soil can control the growth of fungi which may attack seeds. When the soil is treated directly the active compound can be applied in any manner which allows it to be intimately mixed with the soil such as by spraying, by broadcasting a solid form of granules, or by applying the active ingredient at the same time as drilling by inserting it in the same drill as the seeds. A suitable application rate is within the range of from 0.05 to 20 kg per hectare, more preferably from 0.1 to 10 kg per hectare.

Alternatively the active compound can be applied directly to the plant by, for example, spraying or dusting either at the time when the fungus has begun to appear on the plant or before the appearance of fungus as protective measure. In both such cases the preferred mode of application is by foliar spraying. It is generally important to obtain good control of fungi in the early stages of plant growth as this is the time when the plant can be most severely damaged. For cereal crops such as wheat, barley and oats it is often desirable to spray the plant at or before growth stage 5 although additional treatments by spraying when the plant is more mature can augment resistance to the growth or spread of fungi. The spray or dust can conveniently contain a pre- or post-emergence herbicide if this is thought necessary. Sometimes, it is practicable to treat the roots of a plant before or during planting, for example, by dipping the roots in a suitable liquid or solid composition. When the active compound is applied directly to the plant a suitable rate of application is from 0.01 to 10 kg. per hectare, preferably from 0.05 to 5 kg per hectare.

The invention is illustrated in the following Examples. Structures of isolated novel compounds were confirmed by elemental and/or other appropriate analyses.

EXAMPLE 1

2-(2-Carboxyphenyl)acetic acid (9 g) and 4-chloroaniline (6.3 g) in mesitylene (200 ml) were heated at reflux for 18 h, under Dean and Stark conditions. On cooling, the crude product crystallised out and was filtered off. Recrystallisation from ethanol/ethyl acetate gave 2-(4-chlorophenyl)isoquinoline-1,3(2H,4H)-dione, m.p. 178°–180° C. A mixture of this product (2.8 g) and phosphoryl chloride (10 ml) was heated at reflux for 21 h, and excess phosphoryl chloride was then evaporated at reduced pressure. The residue was stirred in ice-water for 4 h, and the precipitate filtered off and suspended in 2% aqueous sodium bicarbonate for 5 minutes. It was again filtered off, taken up in dichloromethane (150 ml) dried and evaporated. Column chromatography of the residue gave a brown solid, which was recrystallised from isooctane/ethyl acetate, to give 3-chloro-2-(4-chlorophenyl)isoquinolin-1(2H)-one m.p. 125°–127° C.

This product (0.58 g), and 1,2,4-triazol-1-ylsodium (0.37 g) were stirred in dry dimethylformamide (10 ml) at 100° C. for 4 h. The mixture was then cooled, poured into water (20 ml) and extracted with dichloromethane. The combined organic extracts were washed with water (20 ml), dried and evaporated. The residue was purified by column chromatography and recrystallised from hexane/ethyl acetate to give 2-(4-chlorophenyl)-3-(1,2,4-triazol-1-yl)-isoquinolin-1(2H)-one, m.p. 154.5°–155.5° C. (Compound 1).

In a similar manner there was obtained in turn
1.
  (a) 2-(2,4-dichlorophenyl)isoquinoline-1,3(2H,4H)-dione, m.p. 168°–169° C.,
  (b) 3-chloro-2-(2,4-dichlorophenyl)isoquinoline-1(2H)-one, m.p. 119.5°–121° C., and
  (c) 2-(2,4-dichlorophenyl)-3-(1,2,4-triazol-1-yl)-isoquinoline-1(2H)-one, m.p. 137°–137.5° C. (Compound 2)
2.
  (a) 2-(2,4,6-trichlorophenyl)isoquinoline-1,3(2H,4H)-dione, m.p. 149.5°–150° C., and
  (b) 3-chloro-2-(2,4,6-trichlorophenyl)isoquinoline-1(2H)-one, which then gave
  (i) 2-(2,4,6-trichlorophenyl)-3-(1,2,4-triazol-1-yl)-isoquinoline-1(2H)-one, m.p. 148.5° C. (decomposes), (Compound 3), and
  (ii) 2-(2,4,6-trichlorophenyl)-3-(imidazol-1-yl)-isoquinoline-1(2H)-one, m.p. 198.5°–199° C., (Compound 4).

EXAMPLE 2

A mixture of 2′,4′-dichloroacetophenone (19.4 g) and selenium dioxide (13.9 g) in pyridine (150 ml) was stirred at reflux for 16 h. After cooling, the insoluble material was removed by filtration and a pyridine solution (30 ml) of o-phenylenediamine (11.1 g) was added to the filtrate. This solution was heated at reflux for 2 hr, cooled and concentrated in vacuo. The residue was stirred with ether (250 ml) and 10% hydrochloric acid (80 ml) and filtered to give 3-(2,4-dichlorophenyl)-quinoxalin-2(1H)-one, m.p. 300° C.(d).

A mixture of this product (9.6 g), phosphoryl chloride (150 ml) and dimethylformamide (5 ml) was heated at reflux for 3 h, cooled and poured onto ice-cold water (1l). After 1 h, the brown solid was removed by filtration to give 2-chloro-3-(2,4-dichlorophenyl)quinoxaline, m.p. 140°–150° C. A mixture of this crude product (6.2 g), 1,2,4-triazole (1.38 g, 0.02 m) and potassium carbonate (2.76 g, 0.02 m) in acetonitrile (150 ml) was stirred at reflux for 18 h. The mixture was filtered whilst warm, and the solid washed with acetonitrile (5.0 ml) and ethyl acetate (50 ml). The filtrate was concentrated in vacuo and the residue was flash chromatographed on silica using petroleum ether (b.p. 60°–80° C.)/ethyl acetate (1:1) as eluent. The product was recrystallised from absolute ethanol and ethyl acetate, to give 3-(2,4-dichlorophenyl)-2-(1,2,4-triazol-1-yl)quinoxaline, m.p. 193°–195° C. (Compound 5).

In a similar manner there was obtained
(a) 3-(2,4-dichlorophenyl)-6,7-dimethylquinoxalin-2-one, m.p. 324°–326° C.(d), which was converted to 2-chloro-3-(2,4-dichlorophenyl)-6,7-dimethylquinoxaline, m.p. 162°–164° C., which was then converted to 3-(2,4-dichlorophenyl)-6,7-dimethyl-2-(1,2,4-triazol-1-yl)quinoxaline, m.p. 173°–176° C. (Compound 6); and
(b) 2-chloro-3-(4-chlorophenyl)quinoxaline, m.p. 169°–170° C., which was converted to 3-(4-chlorophenyl)-2-(1,2,4-triazol-1-yl)quinoxaline m.p. 163°–166° C. (Compound 7). This last reaction was carried out using sodium hydride as the base instead of potassium carbonate.

EXAMPLE 3

In a similar manner to that described in Example 2, 3-chloro-2-(2,4-dichlorophenyl)-2H-indazole was reacted in the presence of potassium carbonate in dimethylformamide
(a) with 1,2,4-triazole, to give 2-(2,4-dichlorophenyl)-3-(1,2,4-triazol-1-yl)-2H-indazole, m.p. 112.5°–113.5° C. (Compound 8), and
(b) with imidazole, to give 2-(2,4-dichlorophenyl)-3-(imidazol-1-yl)-2H-indazole, m.p. 116.5°–118.5° C. (Compound 9).

EXAMPLE 4

2,4-Dichlorophenylacetyl chloride (0.075 mol) was added dropwise over 1 h to a stirred solution of aniline (6.8 g) and triethylamine (7.6 g) in dry ether (200 ml) at 0°-5° C. The reaction mixture was allowed to warm up to room temperature overnight. It was then poured into iced water. An oily layer separated out and gradually solidified. This was recrystallised from diisopropyl ether to give 2-(2,4-dichlorophenyl)acetanilide, m.p. 145.6°-146.5° C.

Phosphoryl chloride (27.6 ml) was added dropwise over 20 minutes to cooled (0° C.) and vigorously stirred dry dimethylformamide (4.95 ml). 2-(2,4-Dichlorophenyl)-acetanilide (12 g) was added and the mixture stirred at 0° C. for 5 minutes and then at 75° C. for 8 h. The cooled reaction mixture was poured into iced water and extracted with ether. The combined ethereal extracts were washed with water, dried and solvent removed in vacuo. Flash chromatography followed by trituration with ether gave 2-chloro-3-(2,4-dichlorophenyl)quinoline, m.p. 120°-122.5° C.

This was then treated with 1,2,4-triazole, in the presence of potassium carbonate in dimethylformamide to give 3-(2,4-dichlorophenyl)-2-(1,2,4-triazol-1-yl)-quinoline, m.p. 157°-158.5° C. (Compound 10)

EXAMPLE 5

A slurry of stannous chloride dihydrate (18 g) in concentrated hydrochloric acid (40 ml) was added slowly at 50° C. to a suspension of 2,4-dichloro-2'-nitrodiphenylamine (5.6 g) in absolute ethanol (50 ml). The temperature rose to 55° C. and the mixture then heated at reflux for 4 hrs. It was then cooled to room temperature and slowly poured into 40% aqueous sodium hydroxide (100 ml), diluted with water and extracted with dichloromethane. The extract was dried, and concentrated in vacuo to give a brown oil which was triturated with petroleum ether (b.p. 40°-60° C.) to give a grey solid. This was filtered and recrystallised from petroleum ether (b.p. 40°-60° C.) to give N-(2,4-dichlorodiphenyl)-o-phenylenediamine, m.p. 62°-64° C. This product (31.9 g) and urea (15.1 g) were heated at 165°-170° C. for 5 h. After cooling, the solid mass was broken up and stirred with water (33 ml) and ether (150 ml). The solid was filtered and recrystallised from ethyl acetate to give 1-(2,4-dichlorophenyl)benzimidazolin-2-one, m.p. 213°-216° C.

A suspension of this product (20 g) in phosphoryl chloride (250 ml) and N,N-dimethylaniline (17.3 g) was heated at reflux for 7 hr. After cooling the excess phosphoryl chloride and N,N-dimethylaniline were removed by distillation in vacuo. The residual oil was poured onto ice/water (1 l) and then extracted with ethyl acetate. dried, and concentrated in vacuo to give a green oil. This was triturated with ether to give a solid which was removed by filtration and the ethereal filtrate was concentrated in vacuo. The residue was chromatographed on silica using dichloromethane as the eluent to give 2-chloro-1-(2,4-dichlorophenyl)benzimidazole, m.p. 80°-83° C.

This was treated with imidazole and potassium carbonate in dimethylformamide as described in Example 1 to give 1-(2,4-dichlorophenyl)-2-(imidazol-1-yl)benzimidazole, m.p. 147°-151° C. (Compound 11).

In a similar manner there was also obtained 1-(2,4-dichlorophenyl)-2-(1,2,4-triazol-1-yl)benzimidazole, m.p. 180°-183° C. (Compound 12).

EXAMPLE 6

A solution of 2-bromo-2'-hydroxyacetophenone (11.25 g) in acetonitrile (25 ml) was added dropwise, with stirring and cooling, to a solution of 1,2,4-triazole (3.45 g) and triethylamine (5.05 g) in acetonitrile (75 ml). The temperature was maintained at −20° C. for 3 hours with continued stirring. The reaction mixture was allowed to warm to room temperature and stirred overnight. The mixture was filtered and the solvent evaporated. The residue was triturated with ethyl acetate and some solid filtered off. The filtrate was chromatographed using ethyl acetate as eluent to give crude 2'-hydroxy-2-(1,2,4-triazol-1-yl)acetophenone. Triethylamine (0.71 g) was added to a solution of this product (1.4 g) in tetrahydrofuran (30 ml). The mixture was stirred at room temperature and 2,4-dichlorobenzoyl chloride (1.45 g) in tetrahydrofuran (20 ml) was added dropwise. The reaction was exothermic and the mixture was stirred at room temperature overnight, then refluxed and stirred for 4 hours. The mixture was cooled, filtered and evaporated. The residue was triturated with diisopropyl ether and filtered to give 2-(2,4-dichlorophenyl)-3-(1,2,4-triazol-1-yl)benzo-1-pyran-4-one, m.p. 226°-228° C. (Compound 13).

In a similar manner, there was obtained 2'-hydroxy-2-(imidazol-1-yl)acetophenone which was converted to 2-(2,4-dichlorophenyl)-3-(imidazol-1-yl)-benzopyran-4-one, m.p. 195°-200° C. (Compound 14).

EXAMPLE 7

4-Chlorobenzaldehyde (1.18 g) was added to 2'-hydroxy-2-(1,2,4-triazol-1-yl)acetophenone, obtained in Example 6 (1.7 g), in dry dimethylformamide (20 ml). The mixture was stirred at 90° C. for 24 hours. It was then poured into ice/water, extracted with dichloromethane and the extract dried and evaporated. The residual oil was triturated with diisopropyl ether to give 2-(4-chlorophenyl)-2,3-dihydro-3-(1,2,4-triazol-1-yl)-benzopyran-4-one, m.p. 140°-141° C. (Compound 15).

EXAMPLE 8

2-Azido-4-chlorobenzoic acid (130 g) was stirred with thionyl chloride (52 ml) in dry toluene at room temperature for 24 hours. The solution was evaporated to give crude 2-azido-4-chlorobenzoyl chloride. This product (14.2 g) was added to a solution of 2,4-dichloroaniline (10.65 g) in dry pyridine (70 ml) and the mixture stirred for 25 mins. It was then poured into ice-water and the precipitate filtered off, washed with water, sucked dry, heated in boiling ethanol and the residue filtered off, washed with ethanol and air-dried to give 2-azido-4-chloro-N-(2,4-dichlorophenyl)benzamide, m.p. 169.5° C. (dec.)

This product (18.43 g) was heated under reflux in thionyl chloride (60 ml) for 22 hours. Excess thionyl chloride was evaporated under reduced pressure and the residue extracted with dichloromethane and worked up to give 3,6-dichloro-2-(2,4-dichlorophenyl)-2H-indazole, m.p. 119.5°-120° C. This was reacted in the presence of potassium carbonate in dimethylformamide in a similar manner to that described in Example 3 with imidazole, to give 2-(2,4-dichlorophenyl)-6-chloro-3-(imidazol-1-yl)-2H-indazole, m.p. 112.5°-113.5° C. (Compound 16).

Test Example

Compounds are assessed for activity against one or more of the following:

*Erysiphe graminis:* barley powdery mildew (EG)
*Plasmopara viticola:* vine downy mildew (PV)
*Botrytis cinerea:* grey mould of tomato (BC)
*Puccinia recondita:* brown wheat rust (PR)

Aqueous solutions or dispersions of the compounds at the desired concentration, including a wetting agent, were sprayed onto the appropriate plant and then inoculated by spraying with spore suspensions of the fungi or by dusting or shaking diseased material over the treated plants for the *E. graminis*. Plants were then kept under controlled environment conditions suitable for maintaining plant growth and development of the disease. After an appropriate time, the degree of infection of the leaf surface was visually estimated.

Compounds were considered active if they gave greater than 50% control of the disease at a concentration of 500 ppm (w/v) or less.

Activities were demonstrated as follows (+ = active).

| Compound No | EG | PR | BC | PV |
|---|---|---|---|---|
| 1 | + | | | |
| 2 | + | + | + | |
| 3 | + | | | |
| 4 | + | | | + |
| 5 | + | + | | |
| 6 | + | | | |
| 7 | + | | | |
| 8 | + | | | |
| 9 | + | + | | + |
| 10 | + | | | |
| 11 | + | | | |
| 12 | + | | | |
| 13 | + | | | |
| 14 | + | | | + |
| 15 | + | | | + |
| 16 | + | + | + | |

We claim:

1. A compound of the formula where
A is oxygen or sulphur;
$R^1$ is phenyl, $C_{1-6}$ alkylphenyl, halo-$C_{1-6}$-alkyl-phenyl, $C_{1-6}$ alkoxy-phenyl, halo-$C_{1-6}$-alkoxy-phenyl or nitrophenyl;
$R^2$ is 1-imidazolyl or 1,2,4-triazol-1-yl; and
$R^3$, $R^4$, $R^5$ and $R^6$, which may be the same or different, are each hydrogen, halo, $C_{1-6}$ alkyl or $C_{1-6}$ alkoxy.

2. The compound of claim 1 where at least two of $R^3$, $R^4$, $R^5$ and $R^6$ are hydrogen.

3. The compound of claim 1 where at least three of $R^3$, $R^4$, $R^5$ and $R^6$ are hydrogen.

4. The compound of claim 1 in which $R^3$, $R^4$ and $R^6$ are hydrogen.

5. The compound of claim 1 where A is oxygen.

6. The compound of claim 1 where $R^1$ is phenyl, 4-chlorophenyl or 2,4-dichlorophenyl.

7. The compound of claim 6 in which A is oxygen and at least two of $R^3$, $R^4$, $R^5$ and $R^6$ are hydrogen.

8. The compound of claim 1 in which $R^2$ is 1-imidazolyl.

9. The compound of claim 1 in which $R^2$ is 1,2,4-triazol-1-yl.

10. The compound of claim 1 which is 2-(2,4-dichlorophenyl)-3-(1,2,4-triazol-1-yl)-isoquinolin-1(2H)-one.

11. The compound of claim 1 which is 2-(4-chlorophenyl)-3-(1,2,4-triazol-1-yl)-isoquinoline-1(2H)-one, 2-(2,4,6-trichlorophenyl)-3-(1,2,4-triazol-1-yl)isoquinoline-1(2H)-one, or 2-(2,4,6-trichlorophenyl)-3-(imidazol-1-yl)-isoquinoline-1(2H)-one.

12. A fungicidal composition which comprises a compound claimed in claim 1 in admixture with an agriculturally acceptable diluent or carrier.

13. A fungicidal composition which comprises a compound claimed in claim 2 in admixture with an agriculturally acceptable diluent or carrier.

14. A fungicidal composition which comprises a compound claimed in claim 4 in admixture with an agriculturally acceptable diluent or carrier.

15. A fungicidal composition which comprises a compound claimed in claim 9 in admixture with an agriculturally acceptable diluent or carrier.

16. A fungicidal composition which comprises a compound claimed in claim 10 in admixture with an agriculturally acceptable diluent or carrier.

17. A fungicidal composition which comprises a compound claimed in claim 11 in admixture with an agriculturally acceptable diluent or carrier.

* * * * *